(12) United States Patent
Caille et al.

(10) Patent No.: US 7,390,926 B2
(45) Date of Patent: Jun. 24, 2008

(54) PROCESS FOR THE DIASTEREOSELECTIVE ALKYLATION OF AN ETHER OXIME OF THE COMPOUND NOPINONE AND NOVEL INTERMEDIATES FOR THE SYNTHESIS OF DIASTEREOSPECIFIC 2-AMINO-NOPINONE DERIVATIVES SUBSTITUTED ON CARBON 3

(75) Inventors: Jean-Claude Caille, Angers (FR); Marc Mauduit, Rennes (FR)

(73) Assignee: ZaCh System, Milan (IT)

( * ) Notice: Subject to any disclaimer, the term of this patent is extended or adjusted under 35 U.S.C. 154(b) by 18 days.

(21) Appl. No.: 11/484,991

(22) Filed: Jul. 12, 2006

(65) Prior Publication Data

US 2007/0225516 A1  Sep. 27, 2007

(30) Foreign Application Priority Data

Mar. 27, 2006 (FR) .................... 06 51054

(51) Int. Cl.
*C07C 249/00* (2006.01)
*C07C 251/00* (2006.01)
*C07C 259/00* (2006.01)
*C07C 291/00* (2006.01)

(52) U.S. Cl. ...................................... 564/256
(58) Field of Classification Search ................. 564/256
See application file for complete search history.

(56) References Cited

FOREIGN PATENT DOCUMENTS

| EP | 290 285 | 5/1988 |
|---|---|---|
| EP | 0 290 285 A2 | 11/1988 |
| EP | 1 069 123 A1 | 3/1999 |
| EP | 1 069 123 | 1/2001 |
| EP | 1 084 711 | 3/2001 |
| EP | 1 084 711 A1 | 3/2001 |
| EP | 1 193 243 | 4/2002 |
| EP | 1 193 243 A1 | 4/2002 |

OTHER PUBLICATIONS

Koval'skaya, S.S., Kozlov, N.G., "cis-4,4,6-Trimethylbicyclo[3.1.1]heptan-2-one in the Synthesis of Nitrogen-containing Bicyclic Compounds", Russian Journal of Organic Chemistry, 36(6), 2000, 785-793, particularly p. 787.*
Kawada et al., "Synthesis of monocyclic analogues of a potent thromboxane receptor antagonist, (±)-(5Z)-7-[3-Endo-[(Phenylsufonyl)Amino]Bicyclo[2.2.1]Hept-2-Exo-yl]Heptenoic Acid (S-145)'," Heterocycles, vol. 28 No. 2, Aug. 1988, p. 573-578. XP009075608.
Blanco et al., "Synthesis of (1'S,3'R)-3-(3'-Amino-2',2'-dimethylcyclobutyl)propan-1-ol from (−−)-β-Pinene," Synthesis, Feb. 1996, p. 281-284. XP-002411914.

K.R. Campos, *A Practical Synthesis for the Core Structure of a Family of Selective Prostaglandin $D_2$ Receptor Antagonists*, J. Org. Chem., 203, 68(6), p. 2338.
D.M. Taylor, *Hydrogen bond interactions of a series of N-substituted $TXA_2$ receptor antagonists*, Chem. Pharm. Bull., 1989, pp. 948-954.
K. Seno, *Thromboxane $A_2$ Receptor Antagonists. II. Synthesis and Pharmacological Activity of 6,6-Dimethyl-bicyclo[3.1.1] heptane Derivatives with the Benzenesulfonylamino Group*, Eur. J. Med. Chem. Ther., 2003, 38(11-12), pp. 1015-1024.
M. J. Martinelli, *Asymmetric Diels-Alder Reactions with γ-Functionalized α,β-Unsaturated Chiral N-Acyloxazolidinones: Synthesis of (+)-S-145*, J. Org. Chem., 1990, 55(17), pp. 5065-5073.
J.M. Blanco, *Synthesis of (1'S,3'R)-3-(3'-Amino-2',2'-dimethylcyclobutyl)propan-1-ol from (−)-β-Pinene*, Synthesis, Feb. 1996, pp. 281-284.
K.Kawada, *Synthesis of Monocyclic Analogues of a Potent Thromboxane Receptor Antagonist*, Heterocycles, vol. 28, No. 2, 1989, pp. 573-578.

* cited by examiner

*Primary Examiner*—Yvonne Eyler
*Assistant Examiner*—Jennifer Y Cho
(74) *Attorney, Agent, or Firm*—Merchant & Gould P.C.

(57) ABSTRACT

The invention provides the diastereoselective alkylation of optically active nopinone to form the compound of formula (I) according to scheme A below:

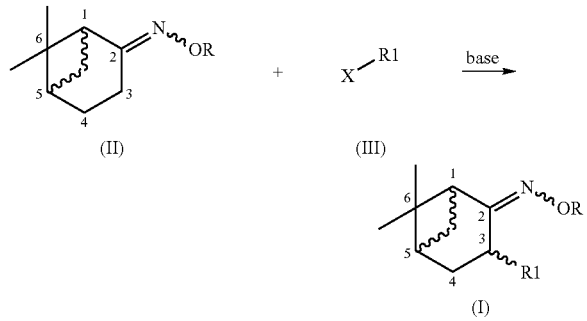

in which:
—R is a $C_{5-15}$ alkyl group;
—R1 is especially a $C_{1-15}$ alkyl, $C_{2-15}$ alkenyl or $C_{2-15}$ alkynyl group or a $C_{5-15}$ aryl, each group optionally being substituted; and
—X is a halogen atom; and
the configuration of the compound of formula (I) is either (E) or (Z) or a mixture of the two.

The compound of formula (I) is a valuable synthetic intermediate.

10 Claims, No Drawings

PROCESS FOR THE DIASTEREOSELECTIVE ALKYLATION OF AN ETHER OXIME OF THE COMPOUND NOPINONE AND NOVEL INTERMEDIATES FOR THE SYNTHESIS OF DIASTEREOSPECIFIC 2-AMINO-NOPINONE DERIVATIVES SUBSTITUTED ON CARBON 3

FIELD OF THE INVENTION

The invention relates to the stereoselective synthesis of an alkylated ether oxime derived from optically active nopinone, of formula (I):

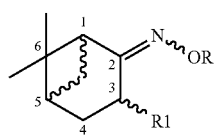
(I)

in which R and R1 are as defined later in the description and the claims.

According to the invention, this stereoselective synthesis is performed via a diastereoselective alkylation process.

STATE OF THE ART

The article published in the journal Heterocycles, 1989, 28(2), pp 573-578 by the authors Tsushima T. and Kawada K. is known from the prior art. It describes a process for the alkylation of a bicyclic oxime using n-butyllithium and an allyl halide as described below:

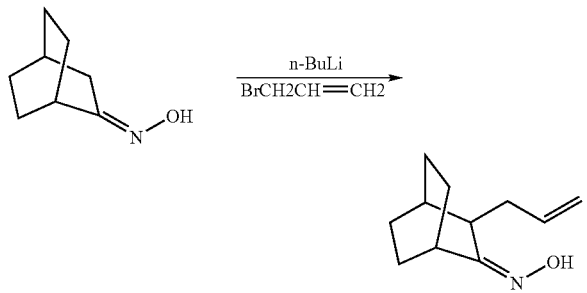

Said process has the disadvantages that it does not effect a stereospecific alkylation and hence gives a mixture of products and dialkylated impurities.

The desired product from the stereochemical point of view therefore requires additional treatments to isolate the correct isomer.

The following may be mentioned among the other processes known from the literature for the synthesis of the compounds of formula (I):

European patent EP 290285 (May 6, 1988) to the Shionogi group describes a two-step process characterized by an alkylation reaction of commercially available (1R)-(+)-nopinone in the presence of n-butyllithium and allyl bromide to give the compound (1R,3RS,5R)-3-(2-propenyl)-6,6-dimethylbicyclo [3.1.1]heptan-2-one, and a methoxyimination reaction in the presence of O-methylhydroxylamine hydrochloride to synthesize the compounds (+)-(1R,3S,5S)- and (+)-(1R,3R,5S)-O-methyloxime-3-(2-propenyl)-6,6-dimethylbicyclo

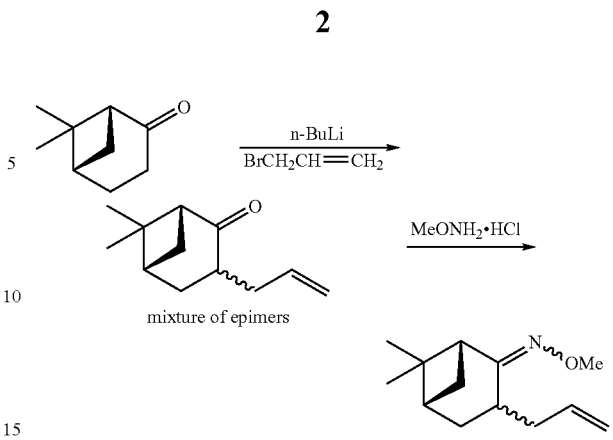

This process gives a mixture of stereoisomers at the carbon in the 3 position and a chemical yield of 66% for the first step. The specific stereochemistry of the final compound is subsequently obtained by means of chromatographic purifications that lead to product losses.

The article published in J. Org. Chem., 2003, 68(6), p. 2338 by the authors Kevin R. C. et al. describes a process for the alkylation of (+)-nopinone using lithium diisopropylamide (LDA) and a propargyl halide derivative. The reaction temperature has a very important effect on the yield and the diastereoselectivity and it is ultimately necessary to carry out a treatment with TFA to avoid epimerization of the final product. The expected product is obtained with a yield of 90% and a diastereoselectivity of 99:1.

European patent EP 1069123 (Mar. 30, 1999) to the Shionogi group describes a process for the synthesis of the compound [(1R,3R,5S)-2-methoxyimino-10-norpinan-3-yl] acetate from another commercially available starting material, (1R)-(−)-myrtenol, by carrying out a Claisen rearrangement reaction in the presence of triethyl orthoacetate under the action of heat, followed by an oxidation reaction of the methylene group in the presence of ozone in order to introduce the carbonyl group, and finally a methoxyimination reaction in the presence of O-methylhydroxylamine hydrochloride according to the scheme below:

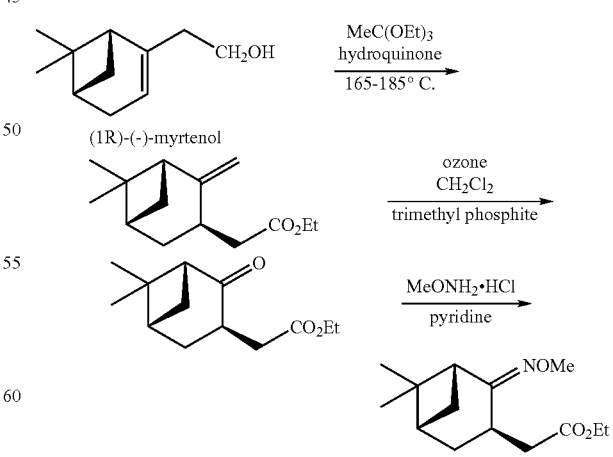

This process is restrictive as from the first step since it is carried out at a very high reaction temperature that requires special industrial equipment.

OBJECTS OF THE INVENTION

One main object of the present invention is to solve the novel technical problem that consists in the provision of a process for the diastereoselective alkylation of an ether oxime of the compound nopinone that avoids the separation of diastereoisomeric compounds in order to obtain the correct isomer.

Another main object of the present invention is to solve this novel technical problem by the provision of a process that improves the productivity of the manufacture of the key intermediates for the synthesis of agonist molecules specific for the prostaglandin D2 receptor, as described in the article published in J. Org. Chem., 2003, 68(6), page 2338.

Another main object of the present invention is to solve this novel technical problem by means of a solution which affords the desired stereospecific compound with a quantitative yield and hence, in particular, affords the synthesis of a family of 2-aminonopinone compounds substituted on carbon 3 with a diastereoisomeric excess in the order of 100% and a high overall yield.

DETAILED DESCRIPTION OF THE INVENTION

The present invention solves all the aforementioned technical problems for the first time in a simple, safe and reliable manner that can be used on the industrial and commercial scale, particularly in the pharmaceutical industry.

Thus, according to a first feature, the present invention provides a process for the diastereoselective alkylation of optically active nopinone to form the compound of formula (I) according to scheme A below:

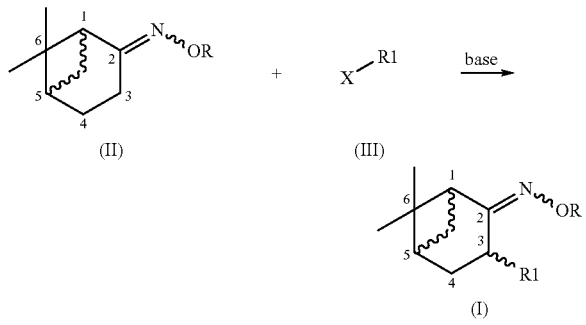

in which:
R is a $C_{1-15}$ alkyl group;
R1 is a $C_{1-15}$ alkyl, $C_{2-15}$ alkenyl or $C_{2-15}$ alkynyl group or a $C_{5-15}$ aryl, it being possible for said alkyl, alkenyl and alkynyl groups to be substituted by a $C_{5-15}$ alkyl or a $C_1$-$C_{15}$ alkoxy; an alkyl($C_1$-$C_{15}$) ester group; an alkyl ($C_{1-15}$) aldehyde group; a $C_1$-$C_{15}$ acyl group; a $C_{5-15}$ aryloxy; an arylalkoxy; a silyloxy such as —OSiH(t-Bu)$_2$, —OSi(Me)$_3$, —OSi(Et)$_3$ or —OSi(Ph)$_3$; an alkylcarbonyloxy such as —OC(O)OMe or —OC(O)OEt; a benzylcarbonyloxy such as —OC(O)OBn; or a heterocycloalkoxy such as tetrahydropyranyloxy (-OTHP), 1,4-dioxan-2-yloxy (—OCH$^1$OCH$_2$CH$_2$OCH$_2$—CH$_2$—CH$^1$) or tetrahydrofuranyloxy;
or the group R1 is particularly —CH$_2$CH$_2$—OR2, in which R2 is a $C_{1-15}$ alkyl group; a $C_{5-15}$ aryl; a $C_{1-15}$ alkylaryl; a silyl; an alkylcarbonate; a benzylcarbonate; or a heterocycloalkoxy, it being possible for said groups to be substituted by a $C_1$-$C_{15}$ alkyl or a phenyl, such as —C(Ph)$_3$ or —CH(Ph)$_2$, a halogen atom, particularly the 2,2,2-trichloroethyl group, or an alkoxy, particularly 1-ethoxyethyl, —CH(OCH$_2$CH$_2$Cl)$_2$, 3,4-dimethoxyphenylmethyl (3,4-DMP-M), 2,3,4-trimethoxy-phenylmethyl (2,3,4-TMPM) or 4-methoxyphenylmethyl (4-MPM); and
X is a halogen atom; and the configuration of the compound of formula (I) is either (E) or (Z) or a mixture of the two.

In one advantageous embodiment of the invention, the invention provides a process for the diastereoselective alkylation of optically active (1R)-nopinone according to scheme A1 below:

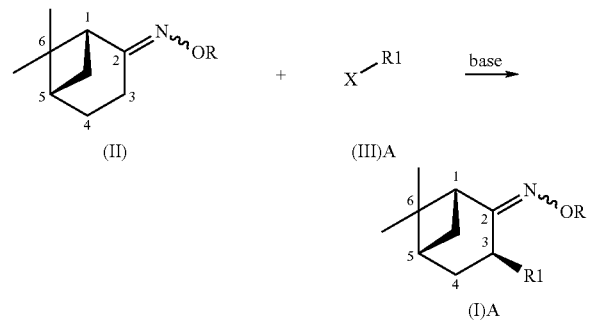

in which R, R1 and X are as defined in the present description and the claims; and the configuration of the compound of formula (I)A is either (E) or (Z) or a mixture of the two.

In yet another advantageous embodiment of the invention, the invention provides a process for the diastereoselective alkylation of nopinone, particularly (1R)-nopinone, in which the group $R^1$ is —CH$_2$CH$_2$—OR2, according to scheme B1 below:

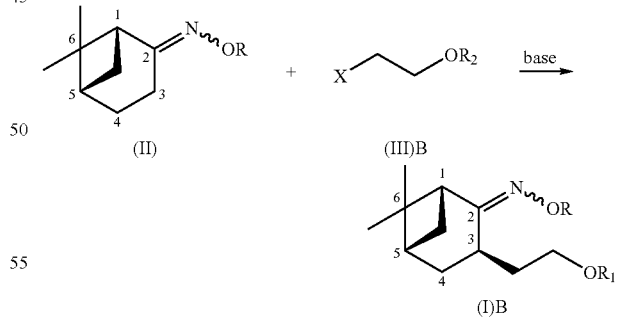

in which R, R2 and X are as defined in the present description and the claims; and the configuration of the compound of formula (I)B is either (E) or (Z) or a mixture of the two.

In one advantageous embodiment of the invention, the $C_{1-15}$ alkyl is selected from methyl, ethyl, propyl, butyl, isobutyl, pentyl, hexyl, octyl, nonyl, decyl, undecyl and dodecanyl; the alkoxy is selected from —OMe, —OC(Me)$_3$, —OC$_2$H$_5$, —OC$_3$H$_7$, —OC$_4$H$_8$, —OC$_5$HR$_{10}$ and —OC$_6$H$_{12}$; the alkyl ester is selected from —CO$_2$Me, —CO$_2$Et and —CO$_2$Ph; the alkyl aldehyde comprises the functional group —CHO at the end of the chain and in particular is —CHO; the acyl group is selected from —COMe, —COEt and —COPh; the aryloxy is selected from —OPh; the arylalkoxy is selected from —OCH$_2$Ph, p-MeOC$_6$H$_4$CH$_2$O—, —OC(Ph)$_3$ and —OCH(Ph)$_2$; the silyloxy is selected from —OSiH(t-Bu)$_2$, —OSi(Me)$_3$, —OSi(Et)$_3$ and —OSi(Ph)$_3$; the alkylcarbonyloxy is selected from —OC(O)OMe and —OC(O)OEt; the benzylcarbonyloxy is selected from —OC(O)OBn; and the heterocycloalkoxy is selected from tetrahydropyranyloxy (—OTHP), 1,4-dioxan-2-yloxy (—OCH$^1$OCH$_2$CH$_2$OCH$_2$CH$_2$—CH$^1$) and tetrahydrofuranyloxy, it being possible for said substituted groups themselves to be substituted by a halogen atom, such as 2,2,2-trichloroethoxy, or an alkoxy, such as 1-ethoxyethoxy, —OCH(OCH$_2$CH$_2$Cl)$_2$, 3,4-dimethoxyphenylmethoxy (3,4-DMPM—O—), 2,3,4-trimethoxyphenylmethoxy (2,3,4-TMPM—O—) or 4-methoxyphenylmethoxy (4-MPM—O—); and X is a halogen atom selected from chlorine, bromine, fluorine and iodine.

The compound of formula (I) is advantageously used for the synthesis of two key intermediates represented by the formulae below, which are used in the synthesis of bicyclic aminoalkyl derivatives as principal components for the synthesis of agonists specific for the prostaglandin D2 (PGD2) receptor:

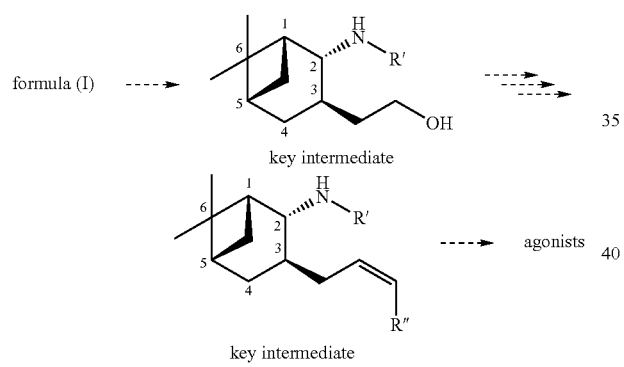

in which, in particular:
R' is a hydrogen atom, an acyl (COR), an ester (Boc) or a sulfonyl (SO$_2$Ar) and
R" is a C$_{1-10}$ alkyl group or a C$_{5-10}$ aryl, it being possible for said groups to be substituted by an alkyl, an alkoxy or an ester or to comprise one or more double or triple bonds.

These molecules, referred to as specific prostaglandin D2 agonists, make it possible to regulate the production of prostaglandin D2, an excess of which leads to cellular dysfunctions that cause allergic problems like conjunctivitis, rhinitis, asthma, urticaria, etc.

For a better understanding of the invention, it is pointed out that the stereochemistry of the compounds is given by way of indication, but does not imply a limitation of the description, the Examples or the claims of the invention.

It is understood from the foregoing that the Applicant has developed a process for the diastereospecific alkylation of an ether oxime of (R)-(+)-nopinone, of formula (II), that affords the compound of formula. (I) with a high diastereospecific excess and a quantitative chemical yield. The compounds of formula (I) are used for the synthesis of compounds derived from 2-aminonopinone substituted on carbon 3, of formula (IV), according to scheme A below:

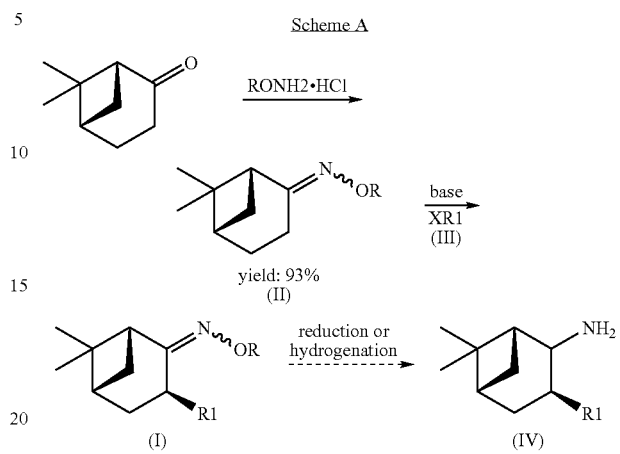

in which R, R1 and X are as defined in the present description and the claims.

More specifically, the Applicant has developed a process for the diastereo-specific alkylation of an ether oxime of R-(+)-nopinone, of formula (II), that affords the compound of formula (I)B with a quantitative chemical yield and the synthesis of novel intermediates of formulae (IV)B, (V)B and (VI)B, obtained with diastereoisomeric excesses above 99% and chemical yields above 90%, according to scheme B below:

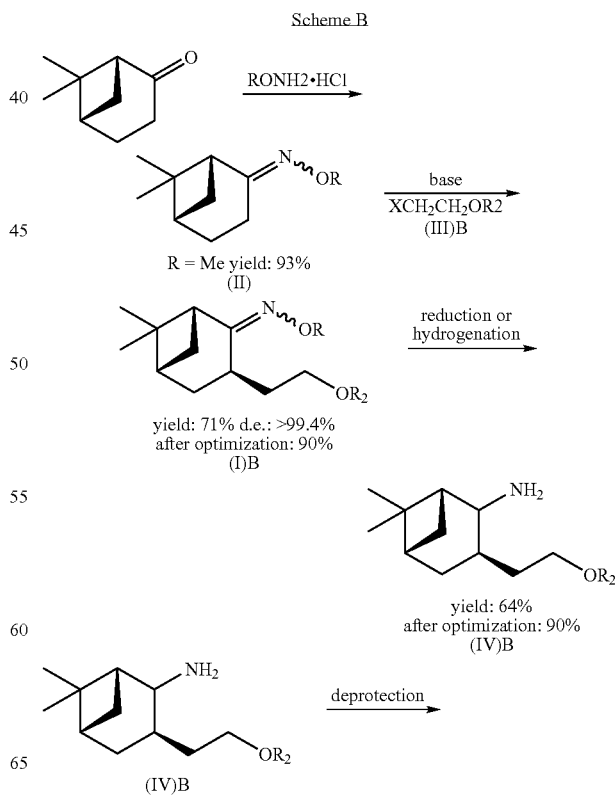

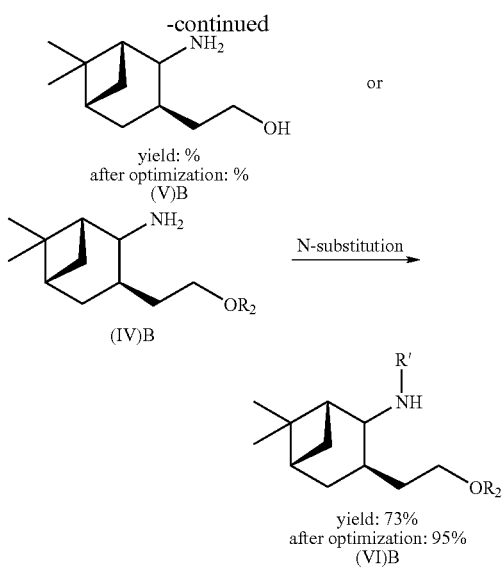

in which:

R is a $C_{1-15}$ alkyl group;

R2 is a $C_{1-15}$ alkyl group (—CH$_3$), a $C_{5-15}$ aryl, a $C_{1-15}$ alkylaryl (—CH$_2$Ph, p-MeOC$_6$H$_4$CH$_2$—), a silyl (—SiH(t-Bu)$_2$, —Si(Me)$_3$, —Si(Et)$_3$, —Si(Ph)$_3$), an alkyl-carbonate (—C(O)OMe, —C(O)OEt), a benzylcarbonate (—C(O)OBn) or a hetero-cycloalkoxy (tetrahydropyranyl (THP), 1,4-dioxan-2-yl (—CH$^1$OCH$_2$CH$_2$OCH$_2$—CH$_2$—CH$^1$) or tetrahydrofuranyl), it being possible for said groups to be substituted by an alkyl (—C(Me)$_3$), a phenyl (—C(Ph)$_3$, —CH(Ph)$_2$), a halogen atom (2,2,2-trichloroethyl) or an alkoxy (1-ethoxyethyl, —CH(OCH$_2$CH$_2$Cl)$_2$, 3,4-dimethoxyphenylmethyl (3,4-DMPM), 2,3,4-trimethoxyphenylmethyl (2,3,4-TMPM), 4-methoxyphenylmethyl (4-MPM), etc.);

X is a halogen atom such as chlorine, bromine, fluorine or iodine; and

R' is a $C_{1-15}$ alkyl group, a $C_{5-15}$ aryl, a $C_{5-15}$ heteroaryl or a $C_{1-15}$ alkylaryl, it being possible for said groups to be substituted by an alkyl, an alkoxy, an acetoxy, a hydroxyl, a halogen, a nitro or a phenyl.

In a first step the process according to the invention follows reaction scheme A1 below:

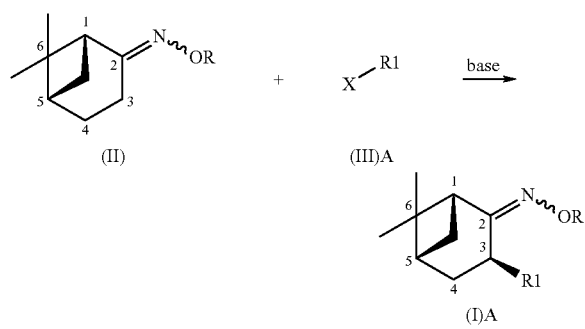

in which R, R1 and X are as defined above.

More specifically, in a first step the process according to the invention follows reaction scheme B1 below:

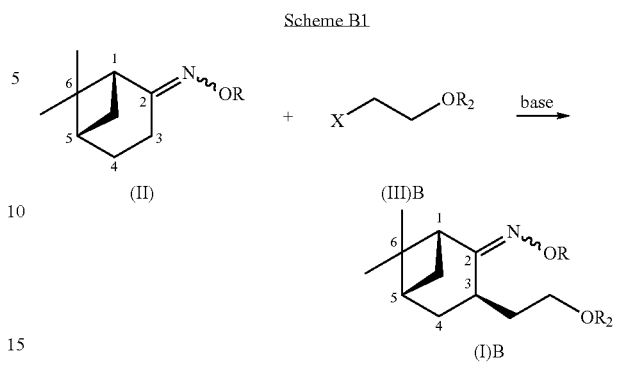

in which R, R2 and X are as defined above.

In one advantageous embodiment of the invention, the base is an alkyllithium derivative such as ethyllithium, n-butyllithium, sec-butyllithium, etc.

The process according to schemes A1 and B1 is advantageously characterized in that, in a first step, a solution of the ether oxime of the compound (R)-(+)-nopinone, of formula (II), in a solvent is reacted with a solution of the base in a solvent, and then, in a second step, the compound of formula (III)A or (III)B is added slowly, according to a procedure known to those skilled in the art, to give the compound of formula (I)A or (I)B.

By way of a non-limiting example, if R2 is an alkyl, the compound of formula (III)B is the methyl ether of 2-bromo-1-ethanol, the methyl ether of 2-iodo-1-ethanol or the benzyl ether of 2-bromo-1-ethanol, and if R2 is a heterocycloalkyl, the compound of formula (III)B is 2-(2-bromoethoxy)tetrahydropyran, 2-(2-iodoethoxy)tetrahydropyran, 2-(2-chloroethoxy)tetrahydropyran or 2-(2-fluoroethoxy)tetrahydropyran.

By way of a non-limiting example, if R$^1$ is an alkyl substituted by an ester, the compound of formula (III)A is the ethyl ester of 2-bromo-1-ethanoic acid or the ethyl ester of 2-iodo-1-ethanoic acid, if R is an alkenyl, the compound of formula (III)A is 3-allyl bromide, and if R is an alkynyl, the compound of formula (III)A is 3-propargyl bromide.

The configuration of the resulting ether oxime of formula (I)A or (I)B can be (E) or (Z) or a mixture of the two.

In one advantageous embodiment, the process is carried out in an organic solvent such as an ether, an aromatic solvent or any other solvent, either pure or in a mixture, that is compatible with the products used in the reaction.

The solvent used in the process of scheme B is preferably tetrahydrofuran (THF).

In another advantageous embodiment, the process according to scheme A1 or B1 is carried out at a temperature of between −75° C. and 0° C. and preferably of −60° C.

The process according to scheme A1 or B1 can be carried out in microreactors, in which the reactants are mixed in small amounts following a course during which ideal properties for carrying out the process, e.g. the ideal temperature or the ideal concentration, are defined.

This technology for carrying out the process according to the invention enables the organometallic compound to be used at a temperature close to 0° C., thereby avoiding the costs of producing cold.

The compound of formula (II)A or (II)B is isolated by the conventional techniques known to those skilled in the art.

The ether oxime of (1R)-nopinone, of formula (II), is prepared from commercially available (1R)-nopinone by a procedure known from the literature, as described in European patent number EP 290285 to the Shionogi group.

In yet another advantageous embodiment, the process of the invention according to scheme B involves a second step characterized in that the compound of formula (I)B is reacted either in the presence of a reducing agent or in the presence of hydrogen and a catalyst to give the compound of formula (IV)B, said step being described by reaction scheme B2 below:

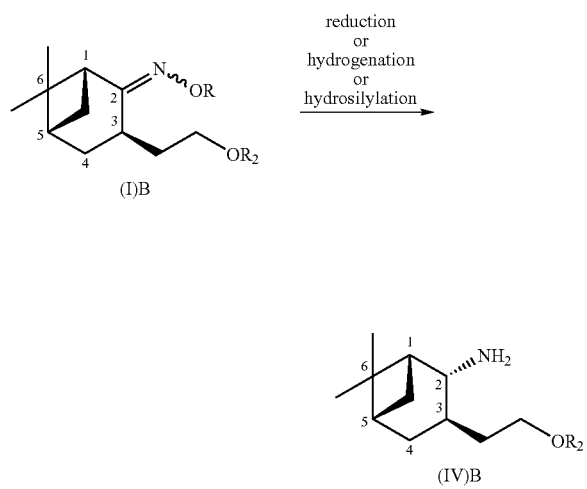

in which the groups R and R2 are as defined above.

In yet another particular embodiment, the process according to scheme B2 is characterized by the reaction of the compound of formula (I)B in the presence of a reducing agent to give the compound of formula (IV)B, and carried out by a procedure known to those skilled in the art.

The reducing agent is advantageously selected from a metal borohydride (NaBH$_4$, KBH$_4$, NaBH$_3$CN, etc.), a hydride (LAH, LiBH$_3$N(Et)$_2$, LiBH$_3$N(i-Pr)$_2$, etc.) and borane in a complexed form that is commercially available or prepared in situ (borane.amine, borane.ether, borane.thioether, etc.).

The chosen reducing agent is preferably the complex BH$_3$.THF.

In yet another particular embodiment, the process according to scheme B2 is characterized by the reaction of the compound of formula (I)B in the presence of a commercially available trialkylsilane, such as trimethylsilane, to give the compound of formula (IV)B, and carried out by a procedure known to those skilled in the art.

Pd/C, Pt/C, Raney nickel, PtO$_2$, etc. may be mentioned, without implying a limitation, as examples of the catalysts used.

In yet another particular embodiment, the process according to scheme B2 is characterized by the reaction of the compound of formula (I)B in the presence of a reducing agent to give the compound of formula (IV)B, and carried out by a procedure known to those skilled in the art.

The process according to scheme B2 is advantageously carried out in an organic solvent such as an ether, an aromatic solvent or any other solvent, either pure or in a mixture, that is compatible with the products used in the reaction. The solvent used is preferably tetrahydrofuran (THF).

The process according to scheme B2 is advantageously carried out at a temperature of between 0° C. and 80° C.

Preferably, the reducing agent used is BH$_3$.THF and the temperature is 0° C.

In yet another particular embodiment, the process of the invention according to scheme B involves a third step B3a characterized in that a reaction for deprotection of the alcohol of the compound of formula (IV)B is carried out to give the compound (V)B, said step being described by reaction scheme B3a below:

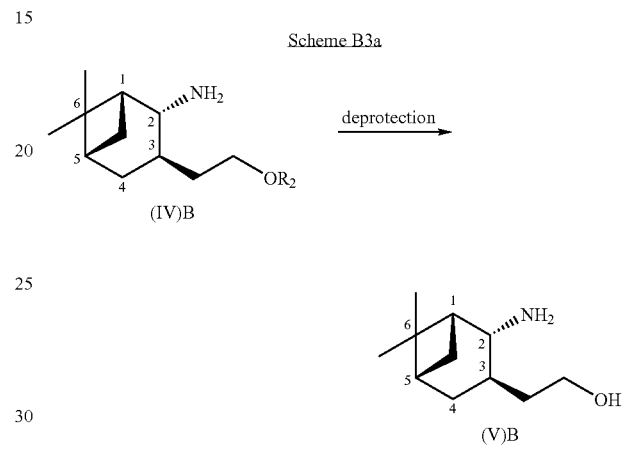

in which the group R2 is as defined above.

In yet another particular embodiment, the process according to scheme B3a is characterized by the reaction of the compound of formula (IV)B in the presence of a reagent that hydrolyzes the ether group, or in the presence of hydrogen and a catalyst, to give the compound of formula (V)B.

Examples which may be mentioned, without implying a limitation, of reactants that hydrolyze the ether group are an organic acid (acetic acid, para-toluenesulfonic acid, etc.) or a mineral acid (HCl, HBr, etc.).

The reaction is advantageously carried out by a procedure known to those skilled in the art or by a procedure such as that described in the article Chem. Pharm. Bull., 1989, pp 948-954.

The reaction according to scheme B3a in the presence of hydrogen can advantageously be carried out with a catalyst selected from supported metals. Pd/C, etc. may be mentioned as examples, without implying a limitation.

The reaction is advantageously carried out by a procedure known to those skilled in the art or a procedure such as that described in the article Eur. J. Med. Chem. Ther., 2003, 38(11-12), pp 1015-1024, or J. Org. Chem., 1990, 55(17), pp 5065-5073.

The process according to scheme B3a is advantageously carried out in an organic solvent such as an ether, an alcohol, an aromatic solvent or any other solvent, either pure or in a mixture, that is compatible with the products used in the reaction.

In yet another particular embodiment of the invention, the process of the invention according to scheme B involves a third step B3b characterized in that the compound of formula (IV)B is reacted in the presence of a compound of formula (VI) to give the compound (VII)B, said step being described by reaction scheme B3b below:

Scheme B3b

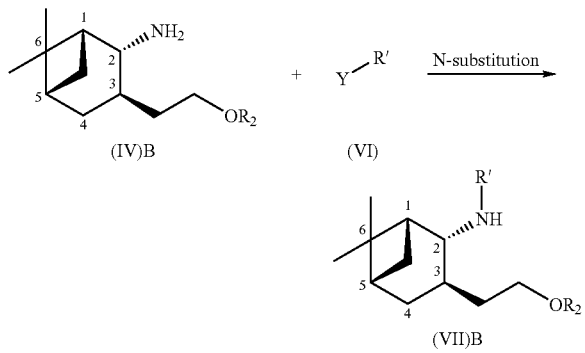

in which the groups R2 and R' are as defined in scheme B and Y is a carboxyl group (—C(O)OH), a halogenocarbonyl (—C(O)X) or a halogenosulfonyl (—S(O)$_2$X), X being as defined above.

In yet another particular embodiment of the invention, the process according to scheme B3b is characterized by the reaction of the compound of formula (IV)B and the compound (VI) by a procedure known to those skilled in the art or a procedure such as that described in patents EP 1084711 (Shionogi), EP 1193243 (Shionogi) and EP 290285 (Shionogi).

The process according to scheme B3b is also advantageously carried out in an organic solvent such as an ether, an alcohol, an aromatic solvent or any other solvent, either pure or in a mixture, that is compatible with the products used in the reaction.

According to a second feature, the present invention covers a novel stereospecific compound of formula (I) below:

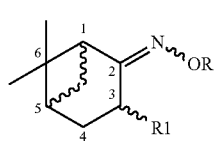

in which R and R1 are as defined in the description and the claims; and the configuration of the compound of formula (I) is either (E) or (Z) or a mixture of the two.

According to a third feature, the present invention covers a novel stereospecific compound of formula (I) or (I)B below:

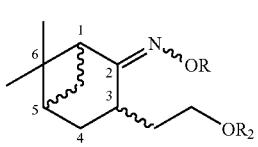

in which R and R2 are as defined in the description and the claims; and the configuration of the compound of formula (I) or (I)B is either (E) or (Z) or a mixture of the two.

According to a fourth feature, the present invention covers a novel stereospecific compound of formula (II):

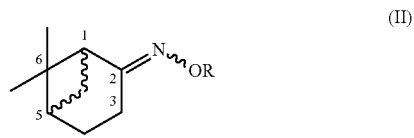

in which R is as defined in the description and the claims.

According to a fifth feature, the present invention covers the use of the compound of formula (I) as defined in the description and the claims, or as obtained by the process according to the invention as defined in the description and the claims, in a process for the reduction of the oxime group according to scheme B2 below:

Scheme B2

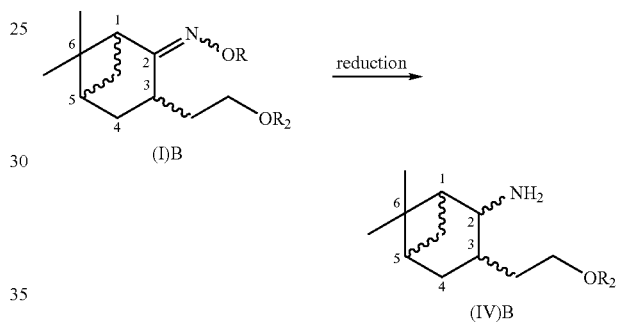

in which R and R2 are as defined above; and the configuration of the compound of formula (IV)B is either (E) or (Z) or a mixture of the two.

According to a sixth feature, the present invention also covers the use of the compound of formula (I) as defined in the description and the claims, or as obtained by the process according to the invention as defined in the description and the claims, in a hydrogenation process according to scheme B2 below:

Scheme B2

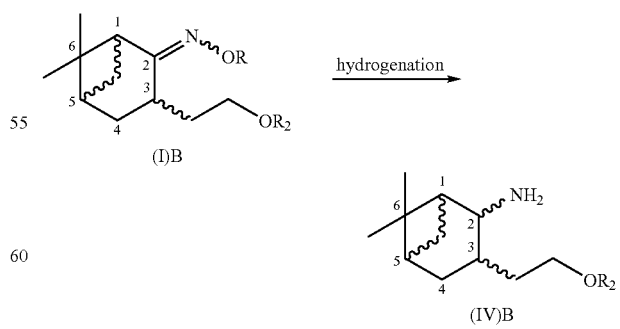

in which R and R2 are as defined above; and the configuration of the compound of formula (IV)B is either (E) or (Z) or a mixture of the two.

According to a seventh feature, the present invention also covers the use of the compound of formula (I) as defined in the description and the claims, or as obtained by the process according to the invention as defined in the description and the claims, in a hydrosilylation process according to scheme B2 below:

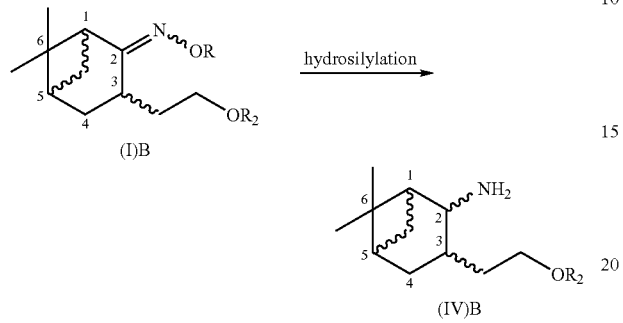

in which R and R2 are as defined above; and the configuration of the compound of formula (IV)B is either (E) or (Z) or a mixture of the two.

According to an eighth feature, the present invention also covers a stereospecific compound of formula (IV)B:

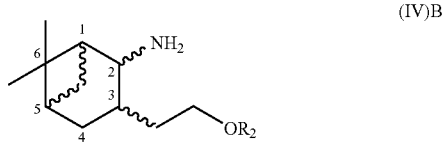

in which R2 is as defined above; and the configuration of the compound of formula (IV)B is either (E) or (Z) or a mixture of the two.

According to a ninth feature, the present invention also covers the use of the compound of formula (IV)B as defined in the description and the claims, or as obtained by the process according to the invention as defined in the description and the claims, in an alcohol deprotection process according to scheme B3a below:

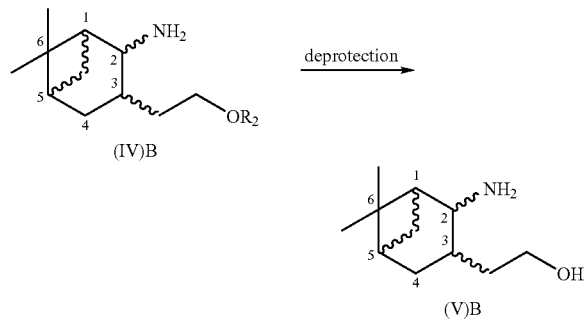

in which R2 is as defined above; and the configuration of the compound of formula (V)B is either (E) or (Z) or a mixture of the two.

According to a tenth feature, the present invention also covers the use of the compound of formula (IV)B as defined in the description and the claims, or as obtained by the process according to the invention as defined in the description and the claims, in an N-substitution process according to scheme B3b below:

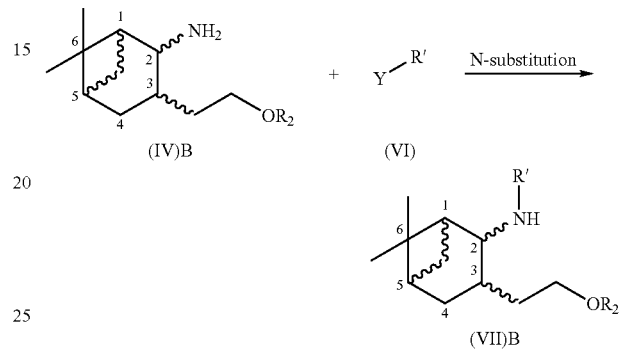

in which R2 is as defined above;

R' is a $C_{1-15}$ alkyl group, a $C_{5-15}$ aryl, a $C_{5-15}$ heteroaryl or a $C_{1-15}$ alkylaryl, it being possible for said groups to be substituted by an alkyl, an alkoxy, an acetoxy, a hydroxyl, a halogen, a nitro or a phenyl; and Y is a carboxyl group (—C(O)OH), a halogenocarbonyl (—C(O)X) or a halogeno-sulfonyl (—S(O)$_2$X), where X is as defined above; and the configuration of the compound of formula (VII)B is either (E) or (Z) or a mixture of the two.

According to an eleventh feature, the present invention also covers a stereospecific compound of formula (VII)B below, or as obtained by the above use:

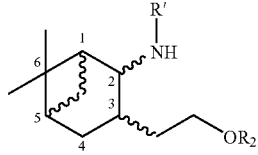

in which R' and R2 are as defined above; and the configuration of the compound of formula (VII)B is either (E) or (Z) or a mixture of the two.

Other objects, characteristics and advantages of the invention will become clearly apparent to those skilled in the art from the following explanatory description referring to a currently preferred embodiment of the stereospecific synthetic process of the invention, which is given by way of illustration and cannot therefore in any way limit the scope of the invention. It is pointed out that any technical characteristic which appears to be novel compared with any STATE OF THE ART is claimed as such in its technical function and as a general technical means, including all equivalent technical means, as will be readily understood by those skilled in the art.

In the Examples the percentages are given by weight, the temperature is given in degrees Celsius and the pressure is atmospheric pressure, unless indicated otherwise.

DESCRIPTION OF THE EXAMPLES OF THE INVENTION

To facilitate understanding, the nomenclature of the products, reagents or solvents is the international nomenclature or that commonly used by those skilled in the art.

Example 1

Formation of the Methylated Oxime of (+)-nopinone

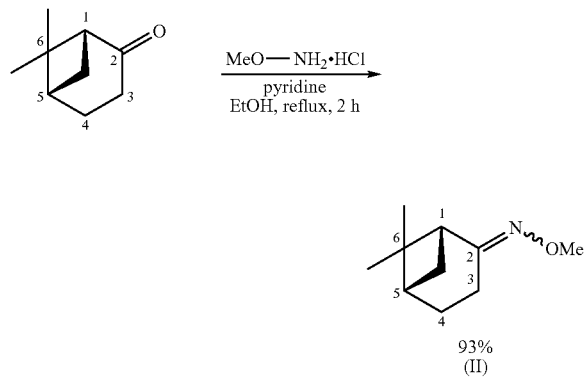

93%
(II)

O-methylhydroxylamine hydrochloride (2.7 g, 1.3 eq., 32.5 mmol), ethanol (30 ml), pyridine (2.64 ml, 1.3 eq., 32.5 mmol) and finally (+)-nopinone (3.52 ml, 1 eq., 25 mmol) are introduced successively into a round-bottom flask fitted with a condenser. The reaction mixture is then refluxed for two hours, with stirring. After evaporation of the ethanol, the residue is dissolved in ethyl ether. The organic phase is washed successively with 1 M hydrochloric acid solution, with water and finally with saturated $NaHCO_3$ solution. The organic phase is subsequently dried over magnesium sulfate and filtered and the solvent is then evaporated off to give 3.9 g (93%) of the methylated oxime of nopinone in the form of a white solid.

Example 2

Alkylation of the Methylated Oxime of (+)-nopinone

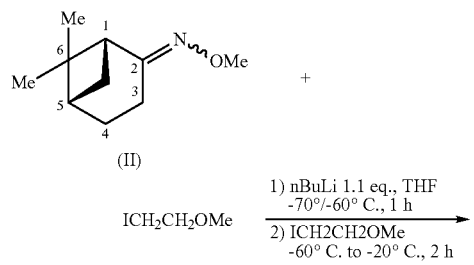

1) nBuLi 1.1 eq., THF
   −70°/−60° C., 1 h
2) ICH2CH2OMe
   −60° C. to −20° C., 2 h

-continued

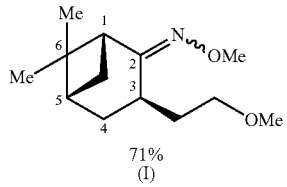

71%
(I)

1.094 g of the methylated oxime 1 (6.55 mmol, 1 eq.) and 60 ml of anhydrous THF are introduced under an argon atmosphere into a Schlenck tube previously dried in an oven. After the reaction medium has been cooled to −70° C., 5 ml of a previously prepared solution of n-BuLi in hexane (c=1.44; 1.1 eq., 7.2 mmol) are added dropwise, the temperature being maintained at between −70° C. and −60° C. After stirring for 1 h at this temperature, 1.34 g of iodoethyl methyl ether (1.1 eq., 7.2 mmol), previously diluted in 20 ml of anhydrous THF, are introduced dropwise over 30 min via a dropping funnel, care being taken to keep the reaction mixture at −60° C. When the addition has ended, the temperature of the reaction medium is raised slowly to −20° C. The reaction medium is analyzed by TLC to ensure the complete disappearance of the starting material (eluent: petroleum ether/AcOEt 9/1). Saturated $NH_4Cl$ solution is then added and the reaction mixture is extracted with ethyl ether. The organic phases are recovered, washed successively with saturated $NaHCO_3$ solution and then with saturated NaCl solution, dried over $MgSO_4$ and filtered. After evaporation of the solvent, the residue (1.7 g) is purified by chromatography on silica gel (eluent: petroleum ether/AcOEt 9/1) to give 1.045 g of the alkylated compound 2 in the form of a colorless oil with a yield of 71%.

Example 3

Reduction of the Methylated Oxime Group to the Corresponding Amine

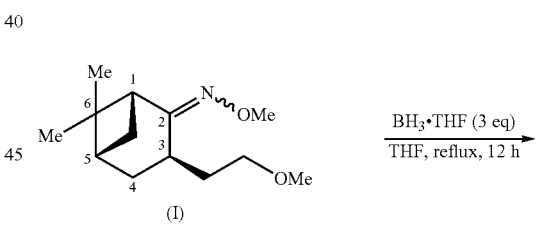

$BH_3$·THF (3 eq)
THF, reflux, 12 h

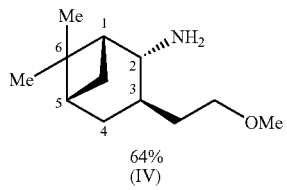

64%
(IV)

The alkylated ether oxime 2 (225 mg, 1 eq., 1 mmol) is dissolved in 10 ml of anhydrous THF in a round-bottom flask fitted with a condenser previously dried under argon. The reaction mixture is then cooled to 0° C. in an ice bath, after which a 1M solution of $BH_3$-THF is introduced dropwise. After the ice bath has been removed, the reaction medium is refluxed for 12 h, with stirring. The reaction mixture is then placed in an ice bath at 0° C., after which a 1M solution of sodium hydroxide is added slowly until the evolution of gas ceases. The reaction mixture is then extracted with ethyl ether. The organic phases are recovered, washed with saturated NaCl solution, dried over magnesium sulfate and filtered. After evaporation of the solvent, the residue (221 mg) is purified by chromatography on silica gel (eluent: MeOH/CH$_2$Cl$_2$ 1/9) to give 125 mg of the desired amine 3 in the form of a white solid with a yield of 64% (not optimized).

Example 4

Synthesis of the Compound of Formula (V)

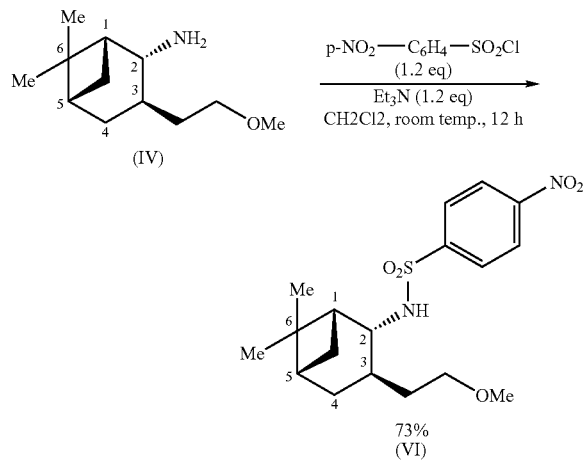

110 mg of the amine 3 (1 eq., 0.56 mmol), anhydrous dichloromethane (10 ml), 148 mg of para-nitrophenylsulfonyl chloride (1.2 eq., 0.67 mmol) and 93 µl of triethylamine (1.2 eq., 0.67 mmol) are introduced successively under an argon atmosphere into a round-bottom flask previously dried in an oven. The reaction mixture is then stirred under an argon atmosphere for 12 hours. A 1M solution of hydrochloric acid is added and the reaction medium is extracted 3 times with ethyl ether. The organic phases are combined, washed successively with water, with saturated NaHCO$_3$ solution and finally with saturated NaCl solution, dried over magnesium sulfate and filtered. After evaporation of the solvent, the residue (200 mg) is purified by chromatography on silica gel (eluent: petroleum ether/AcOEt 8/2) to give 125 mg of the desired protected amine 4 in the form of a white solid with a yield of 73% (not optimized).

What is claimed is:

1. A process for the diastereoselective alkylation of a optically active nopinone to form a compound of formula (I) according to scheme A below:

Scheme A

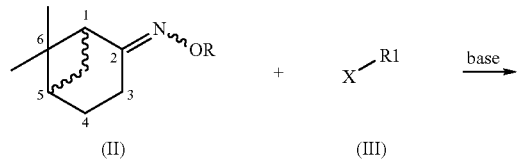

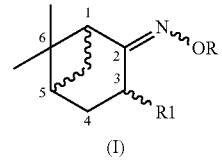

in which:

R is a C$_{1-15}$ alkyl group;

R1 is selected from the group consisting of a C$_{1-15}$ alkyl; a C$_{1-15}$ alkyl substituted by a C$_{1-15}$ alkyl; ; a C$_{1-15}$ alkyl substituted by a C$_1$-C$_{15}$ alkoxy; a C$_{2-15}$ alkenyl; a C$_{2-15}$ alkenyl substituted by a C$_{1-15}$ alkyl; ; a C$_{2-15}$ alkenyl substituted by a C$_1$-C$_{15}$ alkoxy ; a C$_{2-15}$ alkynyl group; a C$_{2-15}$ alkynyl group substituted by a C$_{1-15}$ alkyl; a C$_{2-15}$ alkynyl group substituted by a C$_1$-C$_{15}$ alkoxy; a C$_{5-15}$ aryl; an alkyl(C$_1$-C$_{15}$) ester group; an alkyl(C$_{1-15}$) aldehyde group; a C$_1$-C$_{15}$ acyl group; a C$_{5-15}$ aryloxy; an arylalkoxy; a silyloxy; an alkylcarbonyloxy; a benzylcarbonyloxy; a heterocycloalkoxy; and —CH$_2$CH$_2$—OR2, wherein R2 is is a C$_{1-15}$ alkyl group; a C$_{1-15}$ alkyl substituted by a C$_{1-15}$ alkyl; a C$_{1-15}$ alkyl substituted by a phenyl; a C$_{1-15}$ alkyl substituted by a halogen atom; a C$_{1-15}$ alkyl substituted by an alkoxy; a C$_{5-15}$ aryl; a C$_{1-15}$ alkylaryl; a silyl; a silyl substituted by a C$_{1-15}$ alkyl; a silyl substituted by a phenyl; a silyl substituted by an halogen atom; a silyl substituted by an alkoxy; an alkylcarbonate; an alkylcarbonate substituted by a phenyl ; an alkylcarbonate substituted by an halogen atom; an alkylcarbonate substituted by an alkoxy; a benzylcarbonate; a benzylcarbonate substituted by a C$_{1-15}$ alkyl; a benzylcarbonate substituted by a phenyl; a benzylcarbonate substituted by a halogen atom; a benzylcarbonate substituted by an alkoxy; a heterocycloalkoxy, a heterocycloalkoxy substituted by a C$_{1-15}$ alkyl; a heterocycloalkoxy substituted by a phenyl; and a heterocycloalkoxy substituted by a halogen atom;

X is a halogen atom;

and the configuration of the compound of formula (I) is selected from the group consisting of (E), (Z) and a mixture of (E) and (Z).

2. The process of claim 1, wherein said silyloxy is selected from the group consisting of —OSiH(t-Bu)$_2$, —OSi(Me)$_3$, —OSi(Et)$_3$ and —OSi(Ph)$_3$; said alkylcarbonyloxy is selected from the group consisting of —OC(O)OMe and —OC(O)OEt; said benzylcarbonyloxy is —OC(O)OBn; and said heterocycloalkoxy is selected from the group consisting of tetrahydropyranyloxy (—OTHP), 1,4-dioxan-2-yloxy (—OCH$^1$OCH$_2$CH$_2$OCH$_2$—CH$_2$—CH$^1$) and tetrahydrofuranyloxy.

3. The process of claim 1, wherein said phenyl is selected from —C(Ph)$_3$ and —CH(Ph)$_2$, said alkyl substituted by halogen is a 2,2,2-trichloroethyl group, said alkyl substituted by an alkoxy is selected from 1-ethoxyethyl, —CH(OCH$_2$CH$_2$Cl)$_2$, 3,4-dimethoxyphenylmethyl (3,4-DMPM), 2,3,4-trimethoxyphenylmethyl (2,3,4-TMPM) and 4-methoxyphenylmethyl (4-MPM).

4. The process of claim 1 which is implemented for the diastereoselective alkylation of optically active (1R)-nopinone according to scheme A1 below:

Scheme A1

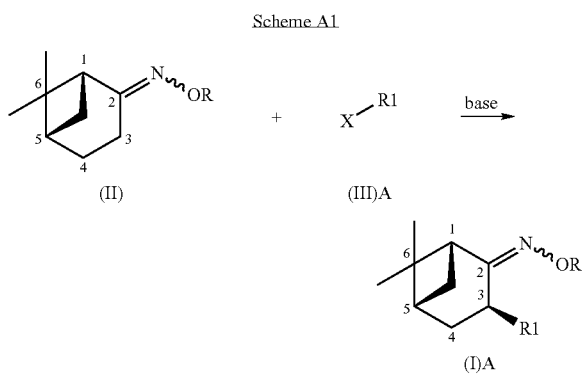

in which R, R1 and X are as defined in claim 1; and
the configuration of the compound of formula (I)A is selected from the group consisting of (E), (Z) and a mixture of (E) and (Z).

5. The process of claim 1 which is implemented for the diastereoselective alkylation of nopinone, in which the group R1 is —CH$_2$CH$_2$—OR2, according to scheme B1 below:

Scheme B1

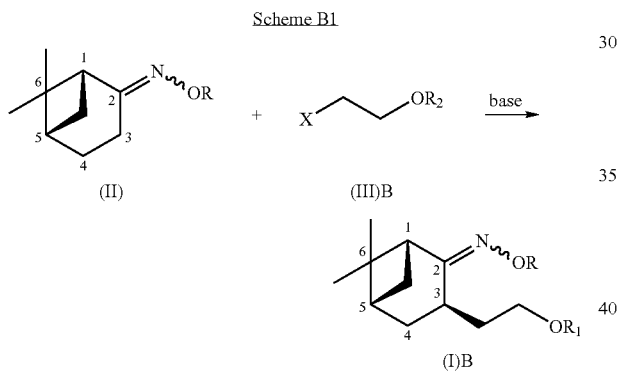

in which R, R2 and X are as defined in claim 1; and
the configuration of the compound of formula (I)B is selected from the group consisting of (E), (Z) and a mixture of (E) and (Z).

6. The process of claim 1 wherein the base is a $C_1$-$C_{15}$ alkyllithium.

7. The process of claim 6, wherein the $C_1$-$C_{15}$ alkyllithium is selected from the group consisting of ethyllithium, n-butyllithium, and sec-butyllithium.

8. The process of claim 1, wherein the temperature is ranging between −75° C. and 0° C.

9. The process of claim 1, wherein the $C_{1-15}$ alkyl is selected from the group consisting of methyl, ethyl, propyl, butyl, isobutyl, pentyl, hexyl, octyl, nonyl, decyl, undecyl and dodecanyl; the alkoxy is selected from the group consisting of —OMe, —OC(Me)$_3$, —OC$_2$H$_5$, —OC$_3$H$_7$, —OC$_4$H$_8$, —OC$_5$H$_{10}$ and —OC$_6$H$_{12}$; the alkyl ester is selected from the group consisting of —CO$_2$Me, —CO$_2$Et and —CO$_2$Ph; the alkyl aldehyde is selected from an alkyl chain with a functional group —CHO at the end of the chain and —CHO; the acyl group is selected from the group consisting of —COMe, —COEt and —COPh; the aryloxy is —OPh; the arylalkoxy is selected from the group consisting of —OCH$_2$Ph, p-MeOC$_6$H$_4$CH$_2$O—, —OC(Ph)$_3$ and —OCH(Ph)$_2$; the silyloxy is selected from the group consisting of —OSiH(t-Bu)$_2$, —OSi(Me)$_3$, —OSi(Et)$_3$ and —OSi(Ph)$_3$; the alkylcarbonyloxy is selected from —OC(O)OMe and —OC(O)OEt; the benzylcarbonyloxy is —OC(O)OBn; and the heterocycloalkoxy is selected from the group consisting of tetrahydropyranyloxy (—OTHP), 1,4-dioxan-2-yloxy (—OCH$^1$OCH$_2$CH$_2$OCH$_2$—CH$_2$—CH$^1$) and tetrahydrofuranyloxy.

10. The process of claim 1, wherein said X is a halogen atom selected from chlorine, bromine, fluorine and iodine.

* * * * *